(12) United States Patent
Neubardt

(10) Patent No.: US 8,087,325 B2
(45) Date of Patent: Jan. 3, 2012

(54) TOOL DEVICE FOR INSERTING FASTENERS

(76) Inventor: Seth L. Neubardt, Mamaroneck, NY (US)

( * ) Notice: Subject to any disclaimer, the term of this patent is extended or adjusted under 35 U.S.C. 154(b) by 396 days.

(21) Appl. No.: 12/460,385

(22) Filed: Jul. 17, 2009

(65) Prior Publication Data
US 2010/0331852 A1 Dec. 30, 2010

Related U.S. Application Data

(60) Provisional application No. 61/269,776, filed on Jun. 29, 2009.

(51) Int. Cl.
*B25B 23/02* (2006.01)
*B65D 85/24* (2006.01)

(52) U.S. Cl. ..................... 81/57.37; 206/347
(58) Field of Classification Search ........... 81/52, 57.37, 81/434; 29/813; 206/338, 347, 349
See application file for complete search history.

(56) References Cited

U.S. PATENT DOCUMENTS

| | | | |
|---|---|---|---|
| 2,266,302 A | 12/1941 | Blair | |
| 4,572,038 A | 2/1986 | Graham | |
| 4,936,169 A | 6/1990 | Parsons | |
| 4,998,452 A * | 3/1991 | Blum | 81/57.37 |
| 5,196,015 A | 3/1993 | Neubardt | |
| 5,474,558 A | 12/1995 | Neubardt | |
| 5,590,574 A | 1/1997 | Lide | |
| 5,690,639 A * | 11/1997 | Lederer et al. | 606/104 |
| 5,735,854 A | 4/1998 | Caron et al. | |
| 6,328,746 B1 | 12/2001 | Gambale | |
| 7,000,509 B2 | 2/2006 | Shiao | |
| 7,028,593 B1 | 4/2006 | Lin et al. | |
| 7,094,239 B1 * | 8/2006 | Michelson | 606/70 |
| 7,104,167 B2 * | 9/2006 | Babij, Jr. | 81/434 |
| 7,134,368 B2 | 11/2006 | Nagy | |
| 7,147,641 B2 | 12/2006 | Chen | |
| 7,237,458 B2 | 7/2007 | Shiao | |
| 7,474,223 B2 * | 1/2009 | Nycz et al. | 340/572.8 |
| 7,931,840 B2 * | 4/2011 | Michelson | 264/162 |
| 2002/0016595 A1 * | 2/2002 | Michelson | 606/73 |
| 2004/0139831 A1 | 7/2004 | Nagy | |
| 2006/0053986 A1 | 3/2006 | Ward | |
| 2006/0243616 A1 * | 11/2006 | Caron | 206/349 |
| 2007/0088362 A1 * | 4/2007 | Bonutti et al. | 606/99 |
| 2008/0281332 A1 * | 11/2008 | Taylor | 606/104 |
| 2009/0125072 A1 * | 5/2009 | Neubardt | 606/305 |
| 2009/0266728 A1 * | 10/2009 | Turner et al. | 206/363 |
| 2009/0308207 A1 * | 12/2009 | Goodhue et al. | 81/57.37 |
| 2010/0289647 A1 * | 11/2010 | Rudduck et al. | 340/572.1 |

* cited by examiner

*Primary Examiner* — David B Thomas
(74) *Attorney, Agent, or Firm* — Law Office of Leo Zucker

(57) ABSTRACT

A tool device includes a frame, a barrel extending from the frame, a first magazine having first passages for containing work or drive bits, and a second magazine having second passages for containing fasteners. A shaft is movable over a path that extends through the barrel. When a second passage is vacant and aligned with a selected first passage, a work bit in the first passage is urged by the shaft through the vacant second passage and through the barrel, to be set at a distal end of the barrel for use on a work object. When a second passage containing a fastener is aligned with a selected first passage, a drive bit in the first passage is urged by the shaft to engage the fastener and advance the fastener to the distal end of the barrel, to enable the bit to drive the fastener into the work object.

8 Claims, 13 Drawing Sheets

TOOL DEVICE FOR INSERTING FASTENERS

CROSS-REFERENCE TO RELATED APPLICATION

This application claims priority under 35 U.S.C. §119(e) of U.S. Provisional Patent Application No. 61/269,776 filed Jun. 29, 2009, titled Tool Device for Inserting Fasteners. The '776 application is incorporated fully herein by reference.

BACKGROUND OF THE INVENTION

1. Field of the Invention

The present invention relates to hand tools, and particularly to a device for fixing fasteners such as screws in various solid objects.

2. Discussion of the Known Art

U.S. Pat. No. 2,266,302 (Dec. 16, 1941) discloses a power driven portable tool that contains a drill and a screwdriver, either of which is selected for use by a mechanism at the tool handle. A number of screws are loaded successively into a supply chute a lower end of which is disposed near the tip of the screwdriver when the screwdriver is retracted. In use, the drill is advanced forward and driven by a motor to form a hole in a workpiece. Once the hole is formed, the drill is retracted and the screwdriver is advanced to engage the head of a screw supplied from the lower end of the chute. The screwdriver is then operated to insert the screw in the hole formed in the workpiece.

U.S. Pat. No. 7,134,368 (Nov. 14, 2006) discloses a screwdriver with a rotatable storage holder having a number of receptacles having axes parallel to the axis of the holder. The receptacles contain individual tool bits. In use, the holder is rotated until a receptacle containing a desired tool bit is aligned with a forward end of a plunger. The plunger is advanced to displace the tool bit out of the storage holder and through a tube attached to the housing, to a presentation position for use at a forward end of tube. The bit is then replaced in its receptacle in the holder by retracting the plunger, according to the patent.

See also, U.S. Pat. No. 7,028,593 (Apr. 18, 2006) and U.S. Patent Application Pub. No. 2006/0053986 (Mar. 16, 2006) which disclose screwdrivers with bit storage cylinders, and U.S. Pat. No. 4,936,169 (Jun. 26, 1990) which discloses a fastener device in which a number of screws are retained in chambers of a cylindrical insert.

My U.S. Pat. No. 5,196,015 (Mar. 23, 1993) and No. 5,474,558 (Dec. 12, 1995) disclose tool systems for inserting pedicle screws in spinal vertebrae of a patient during a surgical procedure. A tool handle is constructed and arranged to accept one of several detachable probes including a first probe for forming a hole in bone tissue, a second probe for threading the formed hole, and a third probe for driving a screw into the threaded hole.

Notwithstanding the known state of the art, there remains a need for a tool that enables a user to form an opening or hole in a work object, to thread the hole if necessary, and to insert and fix a fastener in the hole, all without the need to withdraw the device from the object in order to attach different work probes or bits. In particular, there is a need for a tool device that allows a surgeon to form a hole in bone tissue, to thread the hole and to insert a screw or other fastener, all with the use of only one hand and without needing to withdraw the device from the surgical site until the screw has been properly implanted.

SUMMARY OF THE INVENTION

According to the invention, a tool device includes a frame having first and second magazine chambers aligned with one another, and a barrel that extends from a distal end of the frame. The barrel is formed to receive and position a selected bit or fastener for use at a distal end of the barrel. First and second magazines are constructed and arranged for insertion in corresponding chambers in the frame, including a first magazine having a number of first passages for containing work or drive bits, and a second magazine having a number of second passages for containing fasteners.

A shaft is supported within the frame for movement over a path that extends inside the barrel, and the shaft has an associated handle that is accessible on the device frame. The first and the second magazines are configured so that when inserted in the corresponding chambers, (i) a given first passage in the first magazine can be aligned with a given second passage in the second magazine, and (ii) the aligned first and second passages each receive the shaft when the shaft advances from a retracted position toward the distal end of the frame.

When a second passage in the second magazine is vacant and the vacant passage is aligned with a first passage in the first magazine containing a desired work bit, and the shaft is advanced, the shaft urges the bit to travel through the vacant second passage and through the barrel to position the bit at the distal end of the barrel for use on a work object.

When a second passage in the second magazine containing a desired fastener is aligned with a first passage in the first magazine containing a desired drive bit, and the shaft is advanced, the shaft urges the bit to engage the fastener in the second passage and to advance the bit and the fastener together through the barrel to the distal end of the barrel, thus enabling the bit to drive the fastener into the work object.

For a better understanding of the invention, reference is made to the following description taken in conjunction with the accompanying drawing and the appended claims.

DETAILED DESCRIPTION OF THE INVENTION

Figure 1:
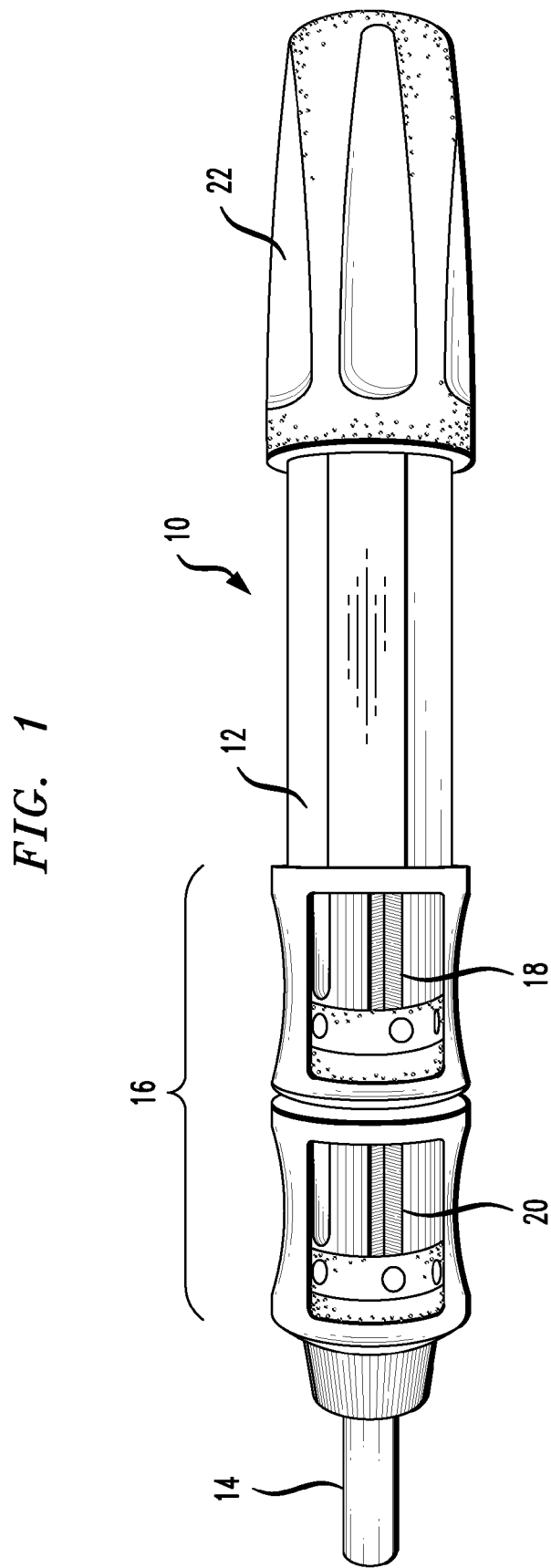
FIG. 1 is a side view of a tool device according to the invention, showing first and second magazines loaded in corresponding chambers in a magazine section of the device.

FIG. 1 is a side view of a tool device 10 according to the invention. The device 10 includes an elongated body frame 12, and a guide tube or barrel 14 that extends from a distal end of the frame 12 as seen at the left of FIG. 1. The frame 12 has a magazine section 16 for retaining and operatively supporting a first magazine 18 and a second magazine 20 in line with one another, when the magazines 18, 20 are inserted in corresponding chambers 30, 32 (see FIG. 2) in the section 16. A cap or handle 22 is accessible at a proximal end of the frame 12, as seen at the right of FIG. 1. The handle 22 is operatively connected to a shaft 46 (see FIG. 4, et seq) supported inside the frame 12 and causes the shaft to slide toward the distal end of the frame when the handle 22 is urged forward from a retracted position.

Figure 2:
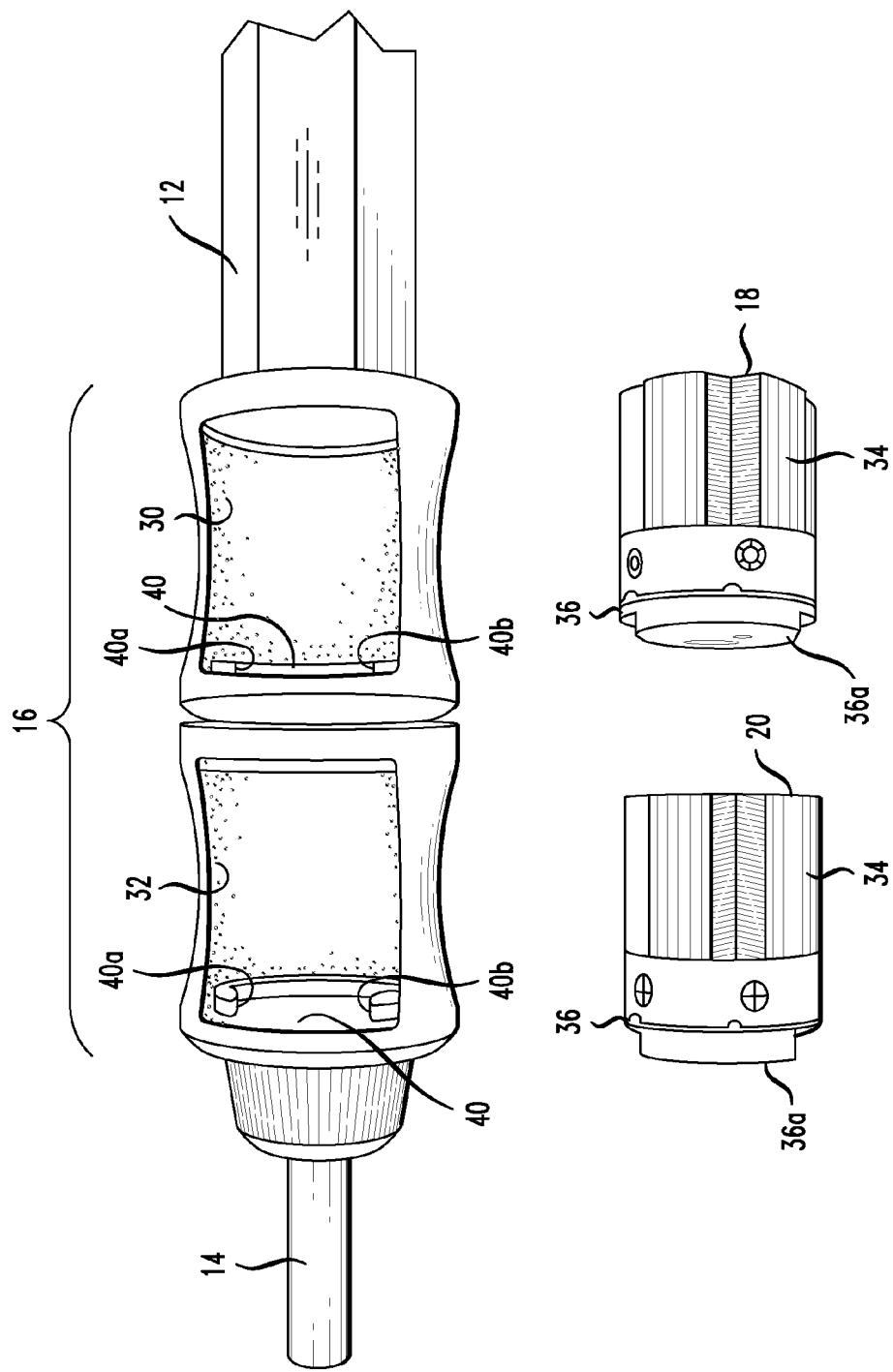
FIG. 2 is an enlarged view of the magazine section of the tool device in FIG. 1, with the two magazines unloaded.

FIG. 2 shows the first and the second magazines 18, 20 removed from the chambers 30, 32 in the magazine section 16. In the illustrated embodiment, each magazine has the same or a similar construction as the rotatable storage holder disclosed in the earlier mentioned U.S. Pat. No. 7,134,368. It will be understood that each magazine may instead be constructed similar to, for example, the revolving cylinder disclosed in U.S. Pat. No. 7,028,593, or the cylinder disclosed in U.S. Patent Application Pub. No. 2006/0053986, both noted earlier. All relevant portions of the mentioned '368 and '593 U.S. patents and the '986 publication are incorporated herein by reference.

Figure 3:
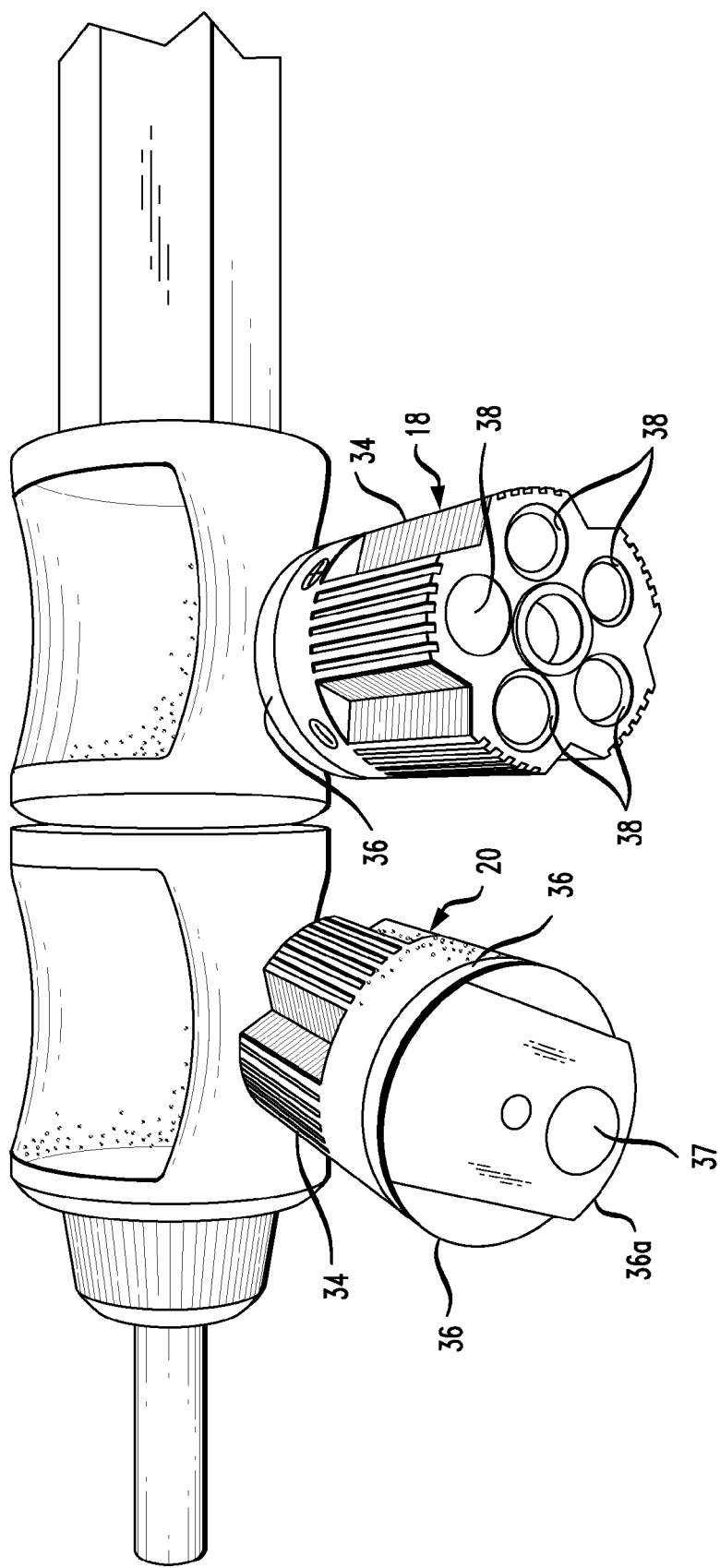
FIG. 3 shows axial end faces of the magazines in FIGS. 1 and 2.

FIG. 3 shows axial and faces of the two magazines 18, 20 in FIG. 2. In the disclosed embodiment, each magazine has a generally cylindrical main body 34, and an end cap 36 that defines a first axial end face of the magazine. The end cap 36 of each magazine is attached to the magazine main body 34 in a known manner that allows a user to turn the body 34 about its axis to a desired position when the magazine is inserted in its chamber with the end cap 36 restrained from rotation with respect to the device frame 12. In the present embodiment, each end cap 36 is formed with a raised area 36a having a generally rectangular perimeter whereby the area 36a slides into a complementary shaped recess 40 (see FIG. 2) in the distal end wall of each magazine chamber 30, 32 when a magazine is inserted. Each recess 40 has side walls 40a, 40b that lock the raised area 36a including the end cap 36 at a fixed position when the main body 34 of the associated magazine is turned to a desired position, as detailed below.

Each magazine end cap 36 also has a through hole 37 formed near its circumference, as seen at the left in FIG. 3. Further, the main body 34 of each magazine 18, 20 has a number of circumferentially spaced through passages 38 that extend axially through the body near its circumference, all of which open at a second axial end face of each magazine as shown at the right in FIG. 3. Thus, a given passage 38 in the main body 34 can be aligned axially with the hole 37 in the associated end cap 36 by turning the main body about its axis relative to the fixed cap. In the disclosed embodiment, the passages 38 in the main body of the first magazine 18 are dimensioned to contain work bits (e.g., drill and tap bits), and drive bits (e.g., screwdriver bits). The passages 38 in the main body of the second magazine 20 are formed to contain fasteners, e.g., screws. Further, during an initial stage of use of the tool device 10, a passage in the second magazine 20 is left empty or vacant as discussed later below.

Figure 4:
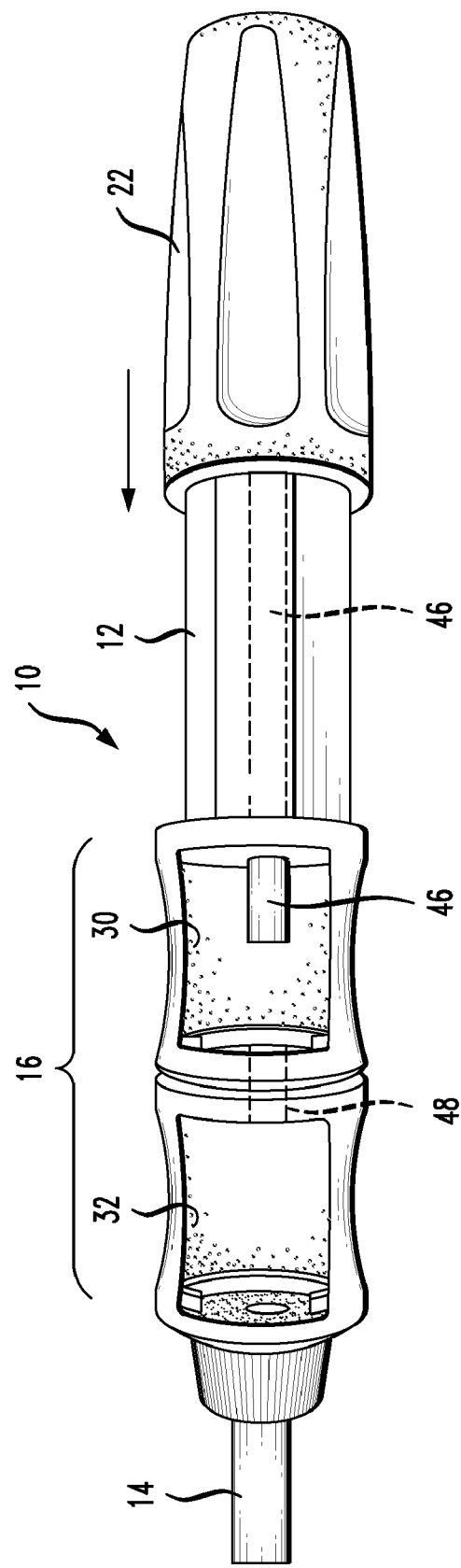
FIG. 4 is a side view of the tool device, showing a distal end of a shaft advancing through the first magazine chamber.
Figure 5:
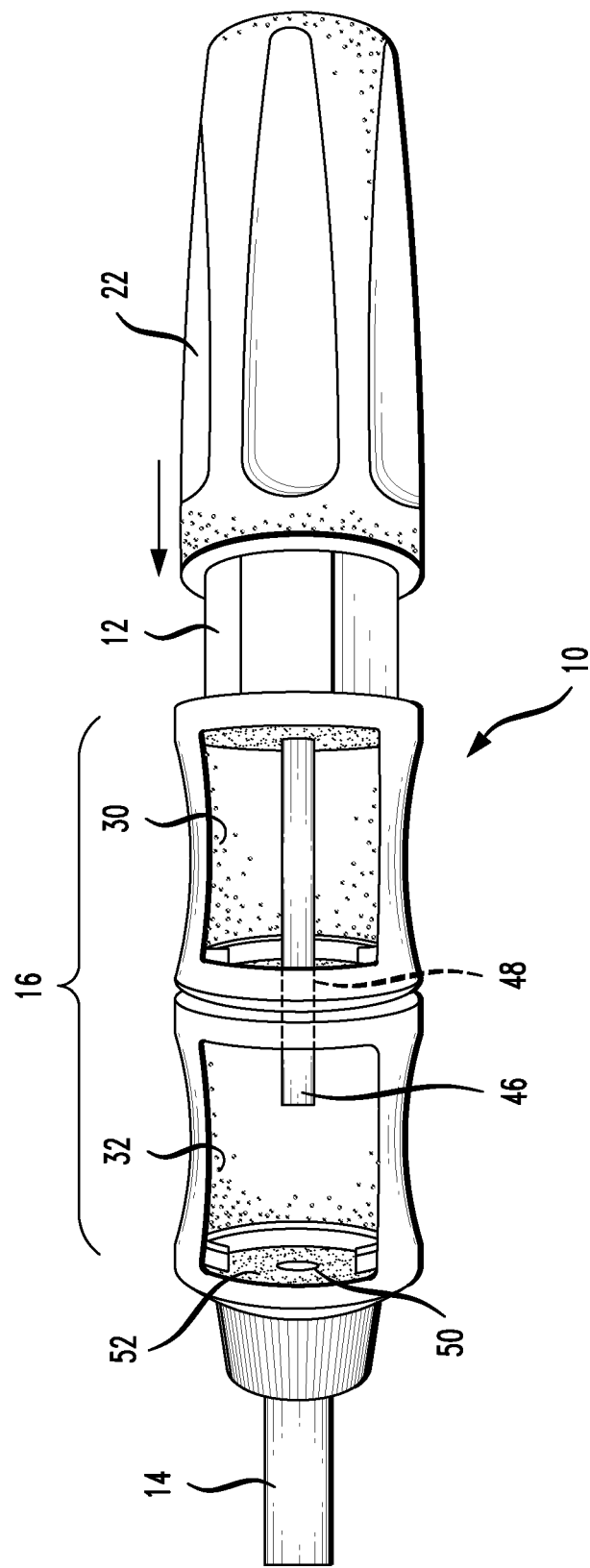
FIG. 5 is a side view as in FIG. 4, showing the shaft advancing through the second magazine chamber.

FIG. 4 is a side view of the device 10 as in FIG. 1, with the magazine chambers 30, 32 exposed to show a distal end of the shaft 46 advancing through the first magazine chamber 30 as the shaft handle 22 is pushed forward from a retracted position. As mentioned, the shaft 46 is supported for axial movement inside the device frame 12 in response to movement of the handle 22. An inter-chamber opening 48 is formed between adjacent end walls of the two chambers 30, 32, in alignment with the path of movement of the shaft 46. Thus, as shown in FIG. 5, the distal end of the shaft 46 will advance through the opening 48 and through the second magazine chamber 32 as the shaft handle 22 continues to move forward. Further, another opening 50 is formed in a distal end wall 52 of the second chamber 32 to allow the path of movement of the shaft 46 to pass through the opening 50 and to extend inside the barrel 14 as the handle 22 continues to advance.

Figure 6:
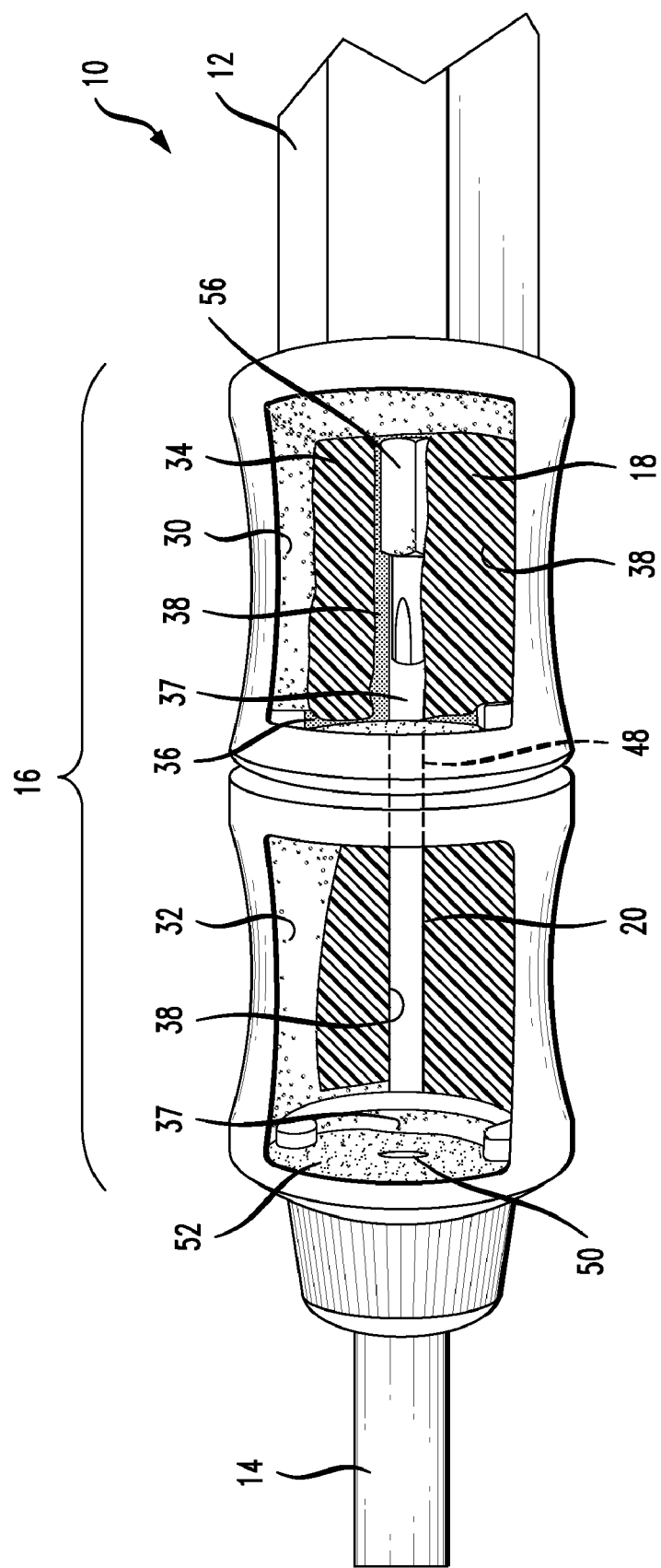
FIG. 6 is a view of the magazine section, with the magazines inserted in their chambers and shown in cross-section, and with a drill bit contained in a passage in the first magazine.

FIG. 6 shows the first and the second magazines 18, 20 in cross section as inserted in the chambers 30, 32 of the magazine section 16, and with the shaft 46 retracted. Note that when the magazines are inserted in the chambers, the hole 37 in the end cap 36 of the first magazine 18 is aligned with the opening 48 between the two chambers, and the hole 37 in the end cap of the second magazine 20 is aligned with the opening 50 in the distal end wall 52 of the second chamber 50. Also note in FIG. 6 that a passage 38 containing a desired drill bit 56 in the first magazine 18 is selected by positioning the main body 34 so that the passage aligns with opening 37 in the end cap 36 of the magazine, and, thus, with the opening 48 between the two chambers.

Further, in FIG. 6, a vacant passage 38 in the second magazine 20 is aligned with the opening 48, and with the opening 50 in the distal end wall 52 of the second chamber 50 through opening 37 in the end cap 36 of the second magazine. Accordingly, when the shaft 46 advances from the retracted position, the shaft enters the first magazine chamber 30 and urges the drill bit 56 in the selected passage 38 of the first magazine 18 to travel through the vacant second passage in the second magazine 20, and through the barrel 14.

Figure 7:
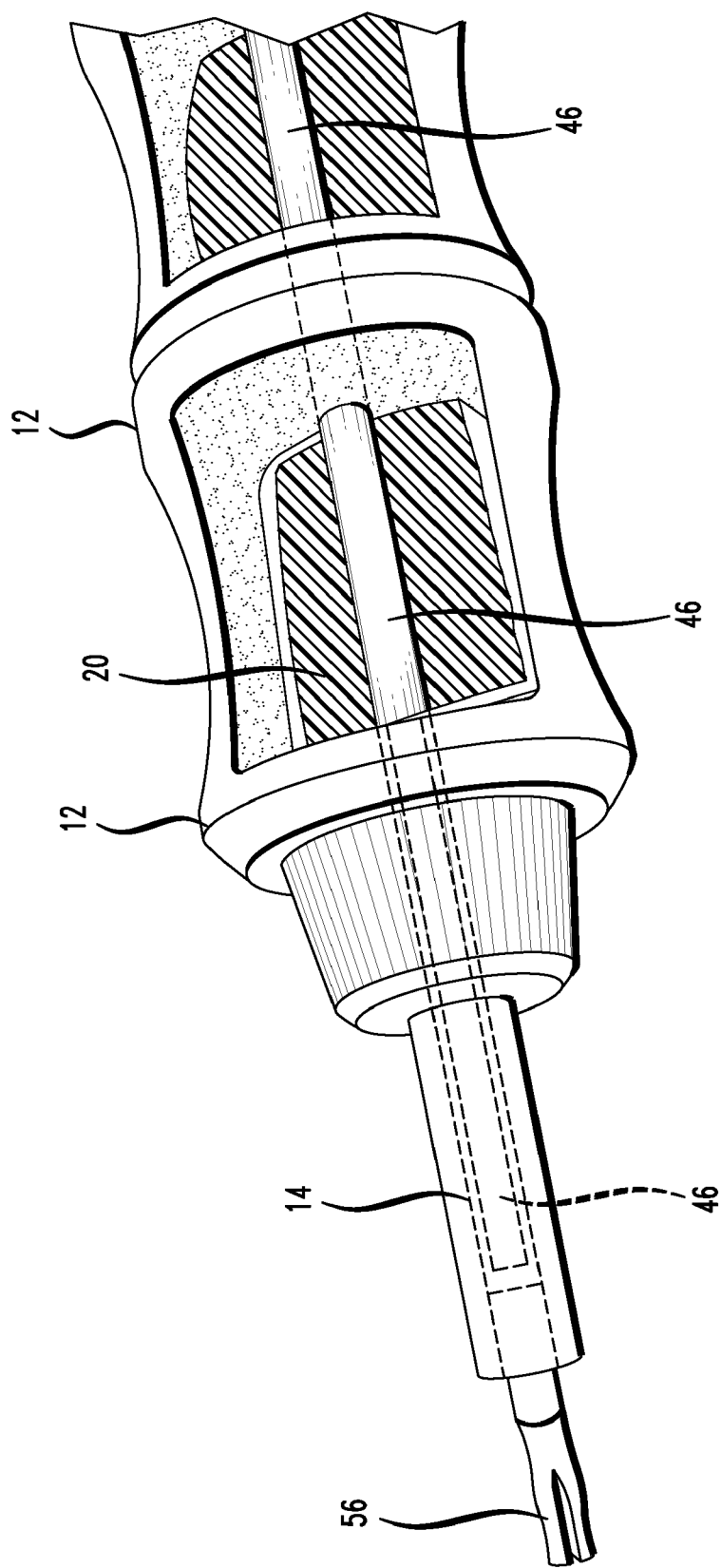
FIG. 7 shows the drill bit in FIG. 6 positioned at a distal end of a barrel of the device, after the bit is advanced by the shaft through a vacant passage in the second magazine and through the barrel.

FIG. 7 shows the drill bit 56 in FIG. 6 after the shaft 46 advances the bit 56 through the vacant passage in the second magazine 20 and the device barrel 14. The drill bit 56 is positioned at a distal end of the barrel 14, and can be used on a work object by turning the device handle 22 manually or by activating an associated power drive (not shown). In the present embodiment, the inner passage of the barrel 14 has, e.g., a hexagonal cross-section, and the neck of drill bit 56 and other bits contained in the first magazine 18 is dimensioned to allow the bit to travel axially through the barrel passage while restraining the bit from rotation relative to the barrel 14. Once the drill bit 56 bores a hole of desired depth in the work object, the bit is withdrawn from the barrel 14 by, for example, retracting the shaft 46 the distal end of which may be magnetically coupled to the neck of the bit 56. When the bit 56 returns to its associated passage 38 in the first magazine 18, the bit is restrained from further rearward movement by, e.g., a partial closure or other known means at the open rear (handle) end of the passage 38. The bit 56 then decouples magnetically from the shaft 46 as the shaft retracts further.

Figure 8:
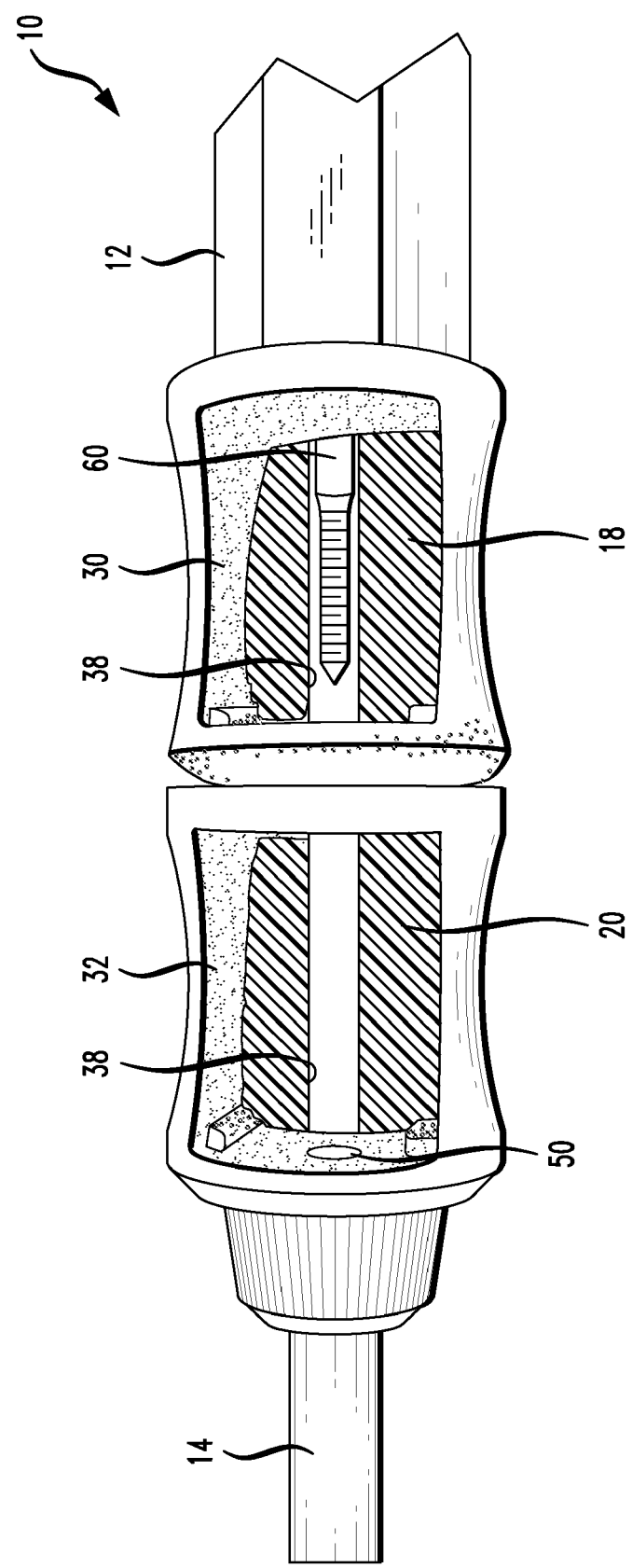
FIG. 8 is a view as in FIG. 6, with the inserted magazines shown in cross-section and a tap bit contained in a passage in the first magazine.

FIG. 8 is a view similar to FIG. 6, showing the magazines 18, 20 in cross-section as inserted in the magazine chambers 30, 32, with the shaft 46 retracted. After the drill bit 56 in FIG. 7 is returned to the first magazine 18, another passage 38 in the first magazine containing a tap bit 60 is selected by rotating the magazine body 34 until the selected passage aligns with the wall opening 48 between the two chambers 30, 32.

The shaft 46 is then advanced to enter the first magazine chamber 30 and urge the tap bit 60 in the selected passage of the first magazine 18 to travel through the vacant second passage in the second magazine 20, and through the barrel 14. The tap bit 60 is then positioned at the distal end of the barrel, and the bit 60 can be used to tap the hole formed in the work object by turning the device handle 22 manually or by activating an associated power drive (not shown). Once the tap bit 60 threads the hole in the work object, the bit is withdrawn from the barrel and replaced in its associated passage in the first magazine 18, as explained above.

Figure 9:
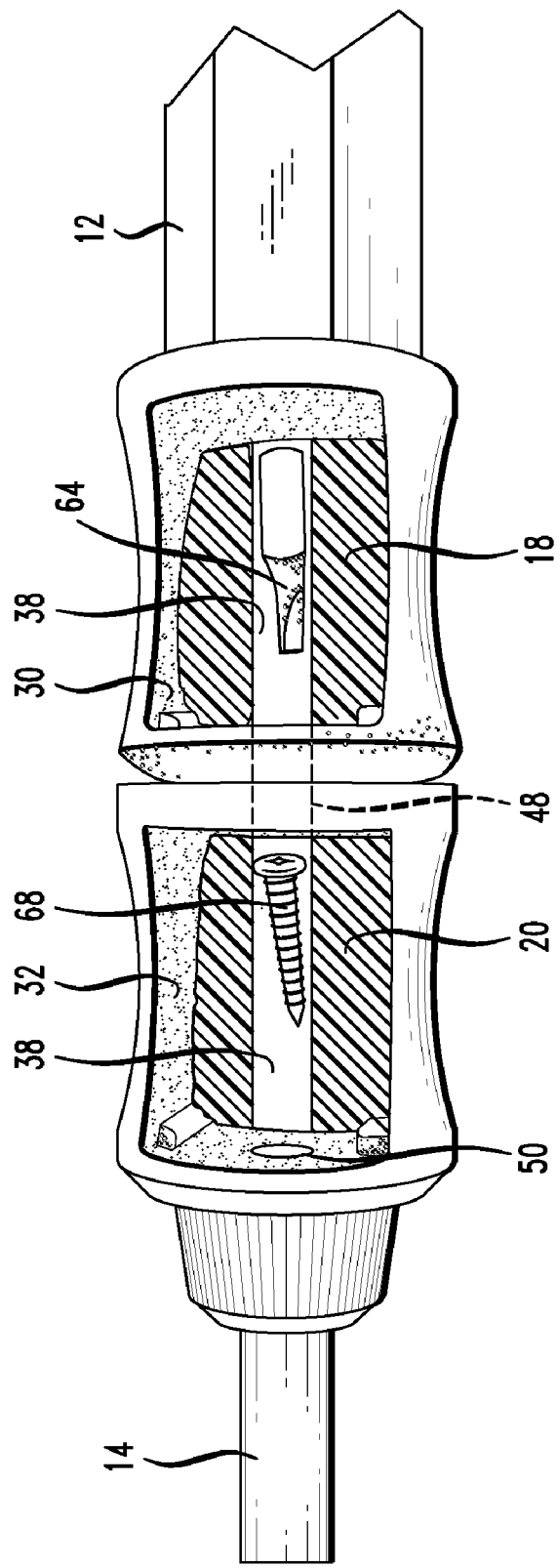
FIG. 9 is a view as in FIG. 6, with the inserted magazines shown in cross-section, showing a drive bit contained in a passage in the first magazine and a screw fastener contained in a passage in the second magazine.

FIG. 9 is a view similar to FIG. 6, showing the magazines 18, 20 in cross-section as inserted in their chambers 30, 32 and with the shaft 46 retracted. After the tap bit 60 in FIG. 8 is returned to the first magazine 18, a first passage 38 in the first magazine 18 containing a drive bit 64 (e.g., a hex screwdriver bit) is selected by rotating the magazine body 34 until the first passage is aligned with the opening 48 between the two chambers 30, 32. A second passage in the second magazine 20 containing a desired fastener 68 (e.g., a screw to be driven by the drive bit 64) is selected by rotating the magazine body until the second passage is aligned with the inter-chamber opening 48 and the opening 50 leading to the device barrel 14.

Figure 10:
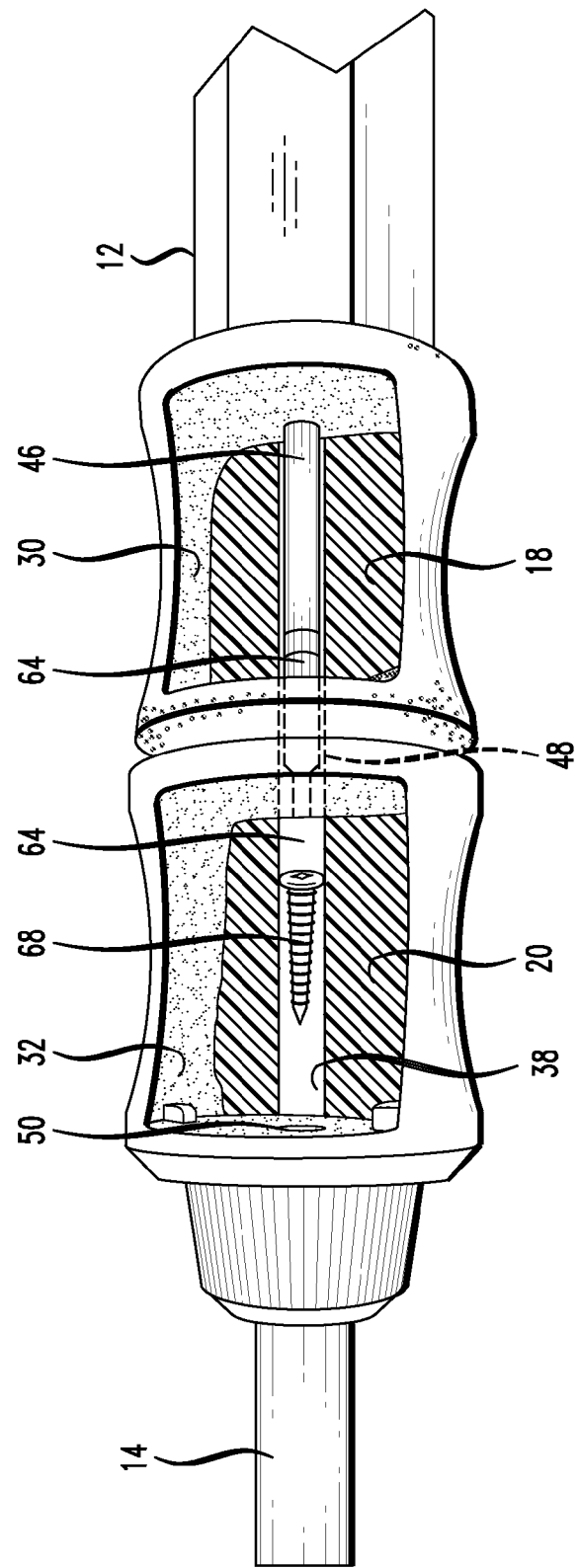
FIG. 10 is a view as in FIG. 9, showing the drive bit engaging the screw fastener by operation of the shaft.

In FIG. 10, the shaft 46 is advanced so that it enters the first chamber 30, urges the drive bit 64 in the first passage in the first magazine 18 through the inter-chamber opening 48 to engage the head of the fastener 68 in the second passage of the second magazine 20, and advances the bit 64 and the fastener 68 together toward the opening 50 leading to the barrel 14.

Figure 11:
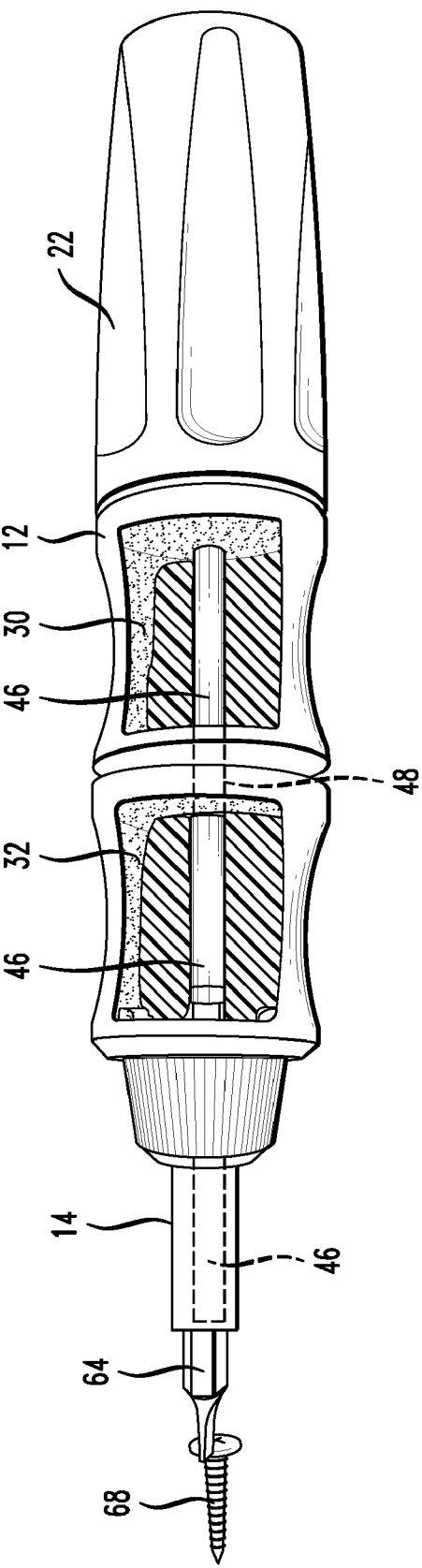
FIG. 11 shows the fastener in FIG. 10 after the shaft advances the drive bit and the fastener together to the distal end of the barrel.

FIG. 11 shows the fastener 68 and the drive bit 64 positioned at the distal end of the barrel 14, after the shaft 46 advances the bit and the fastener through the length of the barrel 14. The tool device 10 can then be used to drive the fastener 68 into a work object using the drive bit 64 a part of which remains seated in the barrel.

Figure 12:
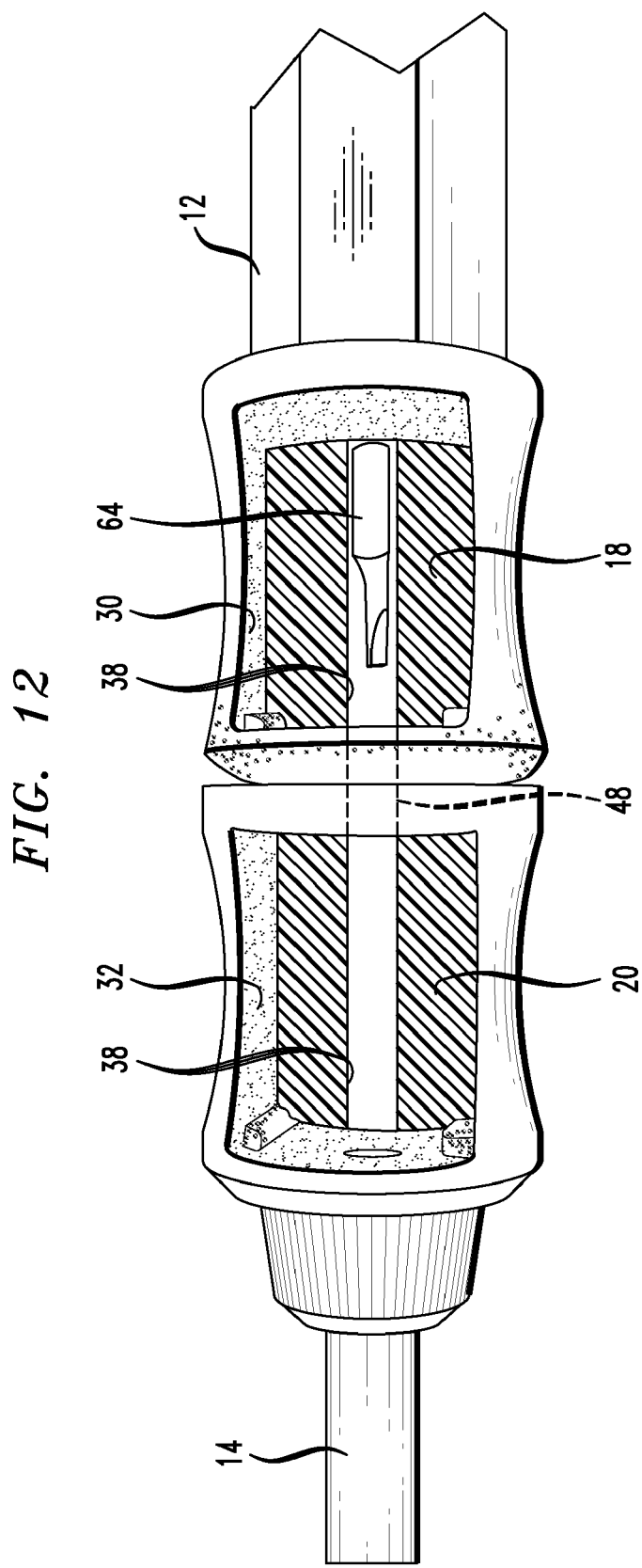
FIG. 12 shows the drive bit in FIG. 11 after the bit is retracted into a passage in the first magazine.

After the fastener 68 is fixed in the work object, the drive bit 64 is retracted by the shaft 46 through the barrel 14 and the passage in the second magazine 20 that was vacated by the fastener 68. The drive bit 64 is then replaced in its associated passage in the first magazine 18 as seen in FIG. 12.

In surgical applications involving the insertion of spinal pedicle or other bone screws, the tool device 10 may also be combined in a known manner with an electrical source operative to supply a nerve stimulating current to a screw selected from the second magazine 20, while the screw is being driven into a bone. The screw may be withdrawn and inserted in a different direction if a monitored patient response indicates that the screw is about to contact a nerve root in the bone. See my earlier mentioned U.S. Pat. No. 5,196,015 (Mar. 23, 1993) and No. 5,474,558 (Dec. 12, 1995), both of which are incorporated fully herein by reference.

As disclosed herein, the tool device 10 is capable of performing a number of tasks on a work object up to and including the insertion of a desired fastener. In surgical applications, the tip of the device barrel 14 can remain at the site of the surgery and need not be withdrawn until a bone screw or other fastener is properly implanted. The second magazine 20 may be pre-loaded with multiple screws or configured for loading of individual screws. In the case of pre-loaded magazines 20, the screw sizes can be clearly identified on the magazine and/or by known RFID techniques. Also, a depth gauge bit may be provided among the bits contained in the first magazine 18, wherein the bit is constructed and arranged to brush the wall of an opening being formed in a patient's bone and detect changes of electrical impedance. The depth measurement may then be used to select a proper length screw.

Figure 13:
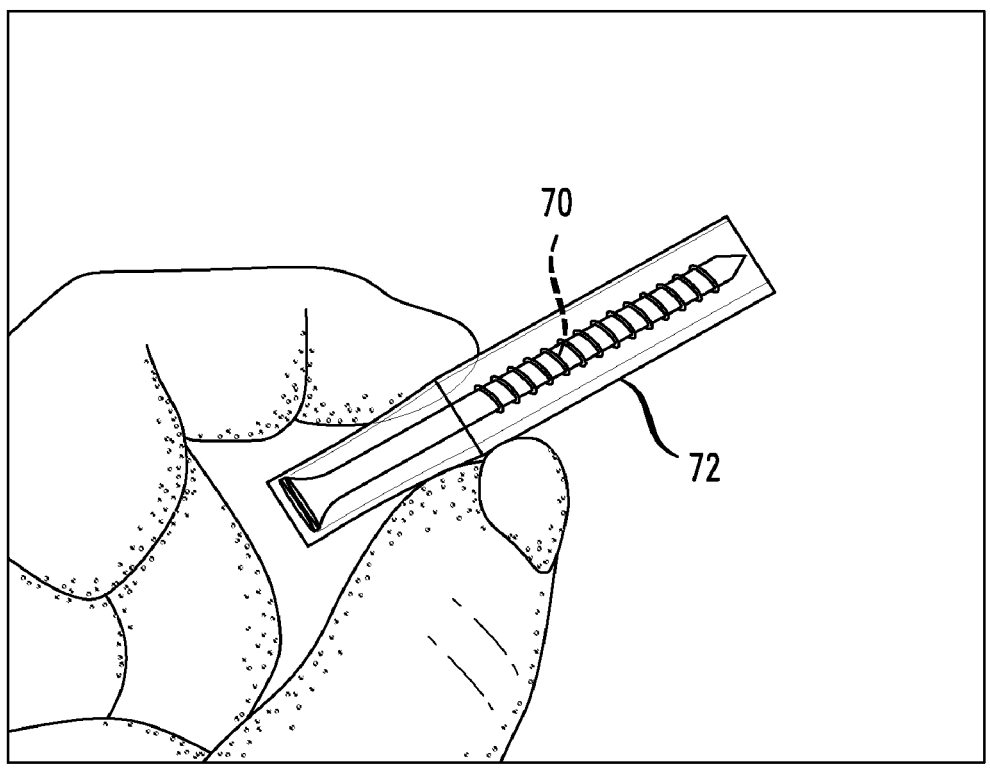
FIG. 13 shows a screw fastener packaged in a case according to the invention.

FIG. 13 shows a surgical screw 70 individually packaged in a cartridge case 72 according to the invention. The case 72 may have a round, square or polygonal profile. A square profile will allow multiple cases 72 to be stackable and efficiently prepackaged. Also, the passages in the second magazine 20 of the tool device 10 may be sized to receive the cases 72. By clearly marking the identification of each screw 70 on its associated case 72, emptied cases remaining after surgery may then be used to identify all screws that have been implanted. An RFID device may also be provided in each case 72, and the tool device 10 equipped in a known manner to sense the RFID device and to display the type and the size of screw contained in the case. Each case 72 may be partially open or otherwise constructed at each axial end of the case, so that a selected drive bit can penetrate one end of the case and urge the tip of the screw 70 out of the opposite end of the case. Surgical screws packaged as described above will thus provide a more accurate screw delivery system for surgeons, as well as better inventory control.

While the foregoing represents preferred embodiments of the invention, it will be understood by those skilled in the art that various modifications and changes may be made without departing from the spirit and scope of the invention, and that the invention includes all such modifications and changes as are within the bounds of the following claims. For example, the inventive tool device may be used by construction workers to insert screws or other fasteners in a variety of applications, as well as by persons or robotic apparatus operating in dangerous environments, for example, earth-orbiting platforms such as a space station or a shuttle.

I claim:

1. A tool device for inserting fasteners in a work object, comprising:
    a body frame including a magazine section having two magazine chambers aligned with one another;
    a barrel extending from a distal end of the frame, wherein the barrel is formed to receive and position a selected bit or fastener for use at a distal end of the barrel;
    two magazines constructed and arranged for insertion in corresponding chambers of the magazine section, including a first magazine having a number of first passages for containing work or drive bits, and a second magazine having a number of second passages for containing fasteners;
    a shaft supported in the frame for movement over a path that extends through the magazine chambers and the barrel, wherein the shaft has an associated handle accessible on the frame; and
    the first and the second magazines are dimensioned and arranged so that when inserted in the magazine chambers, (i) a selected first passage in the first magazine can be aligned with a selected second passage in the second magazine, and (ii) the aligned first and second passages receive the shaft when the shaft advances from a retracted position toward the distal end of the frame by operation of the shaft handle, and so that (a) when a given second passage in the second magazine is vacant and the vacant passage is aligned with a selected first passage in the first magazine and the shaft advances, the shaft urges a work bit in the first passage to travel through the vacant second passage and through the barrel, to position the bit at the distal end of the barrel for use on a work object, and (b) when a second passage in the second magazine containing a fastener is aligned with a selected first passage in the first magazine and the shaft is advanced, the shaft urges a drive bit in the first passage to engage the fastener in the second passage and to advance the bit and the fastener together through the barrel to the distal end of the barrel to enable the bit to drive the fastener into the work object.

2. A tool device according to claim 1, including at least one of an awl bit, a drill bit, a tap bit, and a screwdriver bit contained in corresponding first passages in the first magazine.

3. A tool device according to claim 1, including one or more fasteners contained in corresponding second passages in the second magazine.

4. A tool device according to claim 3, wherein the fasteners comprise screws.

5. A tool device according to claim 4, wherein the screws are bone screws for insertion in bone tissue of a surgical patient.

6. A tool device according to claim 5, wherein the bone screws are spinal pedicle screws.

7. A tool device according to claim 1, wherein at least one of the first and the second magazines comprises a generally cylindrical main body having an axis, and an end cap joined to the main body in a manner that allows the main body to rotate about said axis when the end cap is fixed in a corresponding magazine chamber.

8. A tool device according to claim 1, wherein an inner axial passage of the barrel has a cross-section configured to restrain a part of a bit inside the passage from rotation relative to the barrel.

* * * * *